(12) United States Patent
Kassubek et al.

(10) Patent No.: US 10,215,613 B2
(45) Date of Patent: Feb. 26, 2019

(54) SYSTEM AND METHOD FOR NON-INTRUSIVE AND CONTINUOUS LEVEL MEASUREMENT OF A LIQUID

(71) Applicant: ABB Schweiz AG, Zürich (CH)

(72) Inventors: Frank Kassubek, Rheinfelden (DE); Miklos Lenner, Baden-Dättwil (CH); Tobias Kaufmann, Zürich (CH); Detlef Pape, Nussbaumen (CH)

(73) Assignee: ABB Schweiz AG, Baden (CH)

( * ) Notice: Subject to any disclaimer, the term of this patent is extended or adjusted under 35 U.S.C. 154(b) by 352 days.

(21) Appl. No.: 15/202,185

(22) Filed: Jul. 5, 2016

(65) Prior Publication Data

US 2017/0010146 A1  Jan. 12, 2017

(30) Foreign Application Priority Data

Jul. 6, 2015  (EP) ..................................... 15002010
Nov. 23, 2015  (EP) ..................................... 15195777

(51) Int. Cl.
*G01F 23/296* (2006.01)
*G01N 29/024* (2006.01)
(Continued)

(52) U.S. Cl.
CPC ....... *G01F 23/2962* (2013.01); *G01N 29/024* (2013.01); *G01N 29/222* (2013.01);
(Continued)

(58) Field of Classification Search
CPC .................................................. G01F 23/2962
(Continued)

(56) References Cited

U.S. PATENT DOCUMENTS

| 4,954,997 A | 9/1990 | Dieulesaint et al. |
| 5,015,995 A * | 5/1991 | Holroyd .................. G01F 23/28 340/617 |

(Continued)

FOREIGN PATENT DOCUMENTS

| DE | 68903015 T2 | 5/1993 |
| DE | 19900832 A1 | 7/2000 |

(Continued)

*Primary Examiner* — John Fitzgerald
*Assistant Examiner* — Jean F Morello
(74) *Attorney, Agent, or Firm* — Taft Stettinius & Hollister LLP; J. Bruce Schelkopf (57) ABSTRACT

A system and a method for non-intrusive and continuous level measurement of a liquid enclosed by a solid wall of a vessel. The system comprises an ultrasonic transmitter for generating an ultrasound wave and for emitting it into the vessel wall, an ultrasonic receiver for receiving the ultrasound wave, and an electronic control and data processing unit (ECDU) for controlling operation of the transmitter and of the receiver and for determining the liquid level. The transmitter is able to emit the ultrasound wave as a primary Lamb wave into the vessel wall so that a part of the primary Lamb wave leaks from the vessel wall into the liquid in form of a pressure wave. The ECDU is adapted to repeatedly determine the time of flight of the pressure wave, change the ultrasonic frequency of the transmitter until the determined time of flight reaches a minimum, and determine the liquid level.

20 Claims, 5 Drawing Sheets

(51) Int. Cl.
*G01N 29/22* (2006.01)
*G01S 7/52* (2006.01)
*G01S 7/536* (2006.01)
*G01S 7/539* (2006.01)
*G01S 15/00* (2006.01)
*G01S 15/32* (2006.01)
*G01S 15/88* (2006.01)
*G01B 17/00* (2006.01)
*G01H 5/00* (2006.01)
*G01N 29/04* (2006.01)

(52) U.S. Cl.
CPC .......... *G01S 7/52004* (2013.01); *G01S 7/536* (2013.01); *G01S 7/539* (2013.01); *G01S 15/003* (2013.01); *G01S 15/32* (2013.01); *G01S 15/88* (2013.01); *G01B 17/00* (2013.01); *G01H 5/00* (2013.01); *G01N 29/041* (2013.01); *G01N 2291/011* (2013.01); *G01N 2291/02836* (2013.01); *G01N 2291/02854* (2013.01); *G01N 2291/0427* (2013.01); *G01N 2291/102* (2013.01)

(58) Field of Classification Search
USPC ...................................................... 73/290 V
See application file for complete search history.

(56) References Cited

U.S. PATENT DOCUMENTS 6,234,023 B1*  5/2001  Collins ................... B67C 3/284
                                                          209/524
6,925,870 B2   8/2005  Pappas et al.
7,694,560 B1   4/2010  Dam et al.
2005/0072226 A1* 4/2005 Pappas ................ G01F 23/2962
                                                          73/290 V

FOREIGN PATENT DOCUMENTS

JP   2006322825 A   11/2006
RU      2112221 C1   5/1998

* cited by examiner

SYSTEM AND METHOD FOR NON-INTRUSIVE AND CONTINUOUS LEVEL MEASUREMENT OF A LIQUID

The invention relates to a system and a method for non-intrusive and continuous level measurement of a liquid, where the liquid is enclosed by a solid wall of a vessel.

Level sensors are used to determine the filling level of a vessel containing a liquid. Today, level measurement methods mainly use an intrusive technique which means that an opening in the wall of the vessel is needed to introduce the level sensor into the vessel.

However, in certain industries, such as in the food or pharmaceutical industry, it is undesirable to bring a foreign object into close proximity of or even contact with the liquid, in order to avoid contamination. In even other areas, such as in the chemical or in the oil and gas industry, intrusive level measurement may not be indicated due to the liquids being explosive, easily inflammable, corrosive or being subject to extreme temperatures.

Accordingly, in the past, non-intrusive measurement techniques were developed for measuring the filling level of an unopened vessel. Such non-intrusive sensors may for example be based on X-ray or gamma-ray technology. Since the use of X- or gamma-rays is connected to certain dangers and is therefore not only potentially harmful but also expensive, it is usually applied only if no alternatives exist.

Alternatives are available in the form of acoustic non-intrusive methods. From U.S. Pat. No. 7,694,560B1 and US20100242593A1, ultrasonic level sensors are known where an acoustic signal is sent from underneath the bottom of the vessel towards the level interface and is reflected back the same way. The term "level interface" refers to the surface of the liquid. The ultrasonic signal sent out by these sensors passes directly through the wall of the vessel to enter and to pass the liquid in a straight path in vertical direction. The disadvantage of the measurement methods of U.S. Pat. No. 7,694,560B1 and US20100242593A1 lies in that they require access to the bottom of the vessel or tank, which is often not given in industrial applications.

Figure 1:
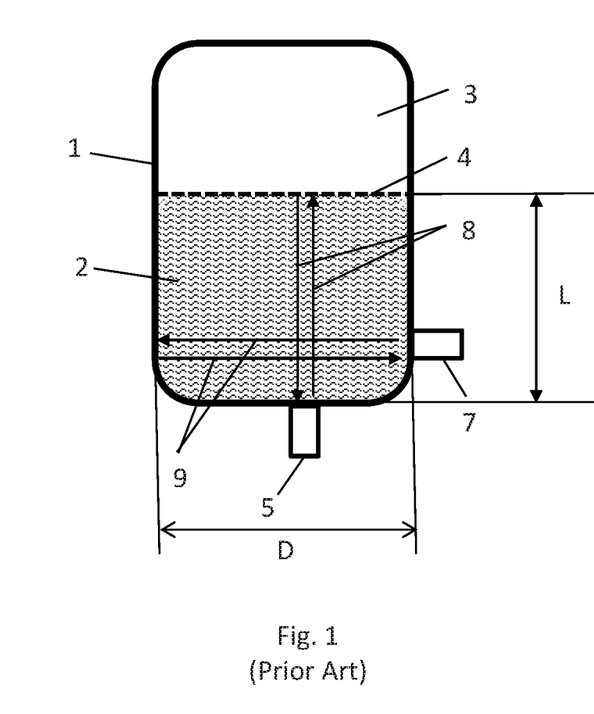
FIG. 1 a side view of a set-up for level measurement in a vessel as previously known, including the measurement of the speed of sound in a liquid.

In JP2006322825A, a non-intrusive liquid level measuring method is described which applies above described level measuring technique. The general setup is shown in FIG. 1. Here, a vessel 1 contains a liquid 2 and a gaseous medium 3 above the liquid 2. The interface between the liquid 2 and the gaseous medium 3 is called liquid surface 4 or level interface. The time of flight of an ultrasonic pulse 8 is measured, where the ultrasonic pulse 8 is transmitted from the outside of the bottom of the vessel 1 by a first ultrasonic transmitter-receiver 5 and reflected back by the liquid surface 4. In order to calculate the filling level of liquid 2, the propagation speed of the ultrasonic wave, i.e. its speed of sound in the liquid 2, is needed. The speed of sound is determined by a second ultrasonic transmitter-receiver 7 which is positioned at a side wall of the tank and which measures the time of flight of a second pulse 9 along the horizontal diameter of the vessel 1. It is required in JP2006322825A that the diameter of the vessel 1 is a known magnitude, so that the speed of sound of the ultrasonic pulse 9 is calculated directly.

In other words, in FIG. 1, an acoustic signal 8 is sent towards the level interface or liquid surface 4, where it is reflected back and then received by the same transducer 5. The time of flight t of the acoustic signal 8 is measured. The distance L from the transducer 5 to the liquid surface 4, and thereby the liquid level, is then calculated by multiplying the propagation speed c_medium of the signal in the liquid 2, which is for acoustical signals the speed of sound, with half the time of flight t, i.e.

$$L=(t \cdot c\_medium)/2 \tag{1}$$

Another non-intrusive solution which is based on the usage of ultrasonic signals directly emitted into the liquid is proposed in U.S. Pat. No. 6,925,870B2. There, a transmitter-receiver is located at the side wall of the vessel. One ultrasonic signal is emitted in horizontal direction and reflected back from the opposite side wall of the vessel. This signal is used for measuring the speed of sound, i.e. the travel speed of the ultrasonic beam, in the liquid. Another ultrasonic signal is emitted in an angular direction in such a way that it is reflected back by the intersection between the liquid surface and the opposite side wall of the vessel. From the time of flight of this second signal, the height of the liquid surface relative to the location of the transducer is determined.

A prerequisite for the method of U.S. Pat. No. 6,925,870B2 to work is that the liquid surface, i.e. the level interface, and the vessel wall describe a rectangular corner. In other words, the method is only applicable to vessels with vertical walls. For non-vertically aligned walls, the ultrasonic signal would not be reflected back to the transmitter but to a different position, depending on the angle of the transmitted beam and the angle of the wall.

A different technology for non-intrusive liquid level measurements is described in DE68903015T2, RU2112221C1and Sakharov et. al., "Liquid level sensor using ultrasonic Lamb waves", Ultrasonics 41 (2003), pp. 319-322. The technology described there is based on the use of ultrasonic Lamb waves propagating along the vessel wall or walls, and is not applicable for continuous measurement of the level height, but instead for detecting whether a predefined level is exceeded by the liquid surface or not. Further, in contrast to the ultrasonic sensors described previously, where the ultrasonic signal is emitted directly into the liquid, the ultrasonic Lamb waves are generated and kept to a large degree inside the wall surrounding the liquid. In other words, while the directly emitted and reflected ultrasonic signals are used by continuous level sensors, the ultrasonic Lamb waves travelling inside the vessel wall are used by point level sensors. Even further, while in the continuous level sensors the ultrasonic signal is reflected back using the same path as the emitted beam so that transmitter and receiver are placed at the same position outside of the vessel wall, the point level sensors have a pair of transmitter and corresponding receiver placed at the same height but at different horizontal positions.

Figure 2:
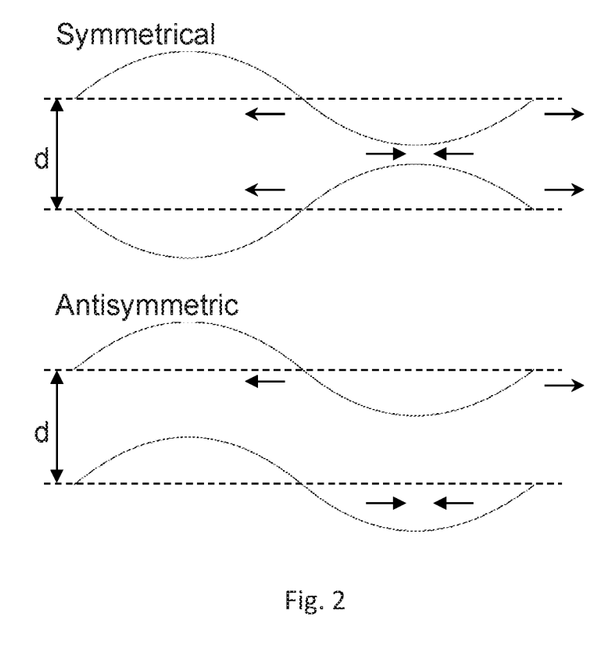
FIG. 2 a schematic behavior of the two zero-order modes of a Lamb wave.

Lamb waves or also called plate waves are mechanical waves generated in plates where the wave propagation is influenced by the reflection of the wave at the sides of the walls and the thus limited propagation space. They thus show similar properties as waves propagating in wave guides. Lamb waves are propagating in different modes with different properties, in particular different propagation velocities as well as different attenuations. Typically at low frequencies, a symmetric S0 and an anti-symmetric or asymmetric A0 mode can occur, which are depicted in FIG. 2. Ideally, the waves are reflected totally at the sides of the plate and are thus kept inside the plate. This is valid in a first approximation for plates in a gaseous medium or in vacuum.

In the case of a contact of the plate with a liquid, the reflectivity of the interface is reduced and the Lamb waves can emit acoustic energy into the surrounding liquid medium. This occurs especially for the asymmetric mode at low frequencies. Due to the emitting of acoustic energy into the surrounding medium, they are also called leaky Lamb waves. This emitting of acoustic energy into the liquid results in a strong attenuation of the wave, which effect is especially used in the point level sensors of DE68903015T2, RU2112221C1 and Sakharov for the detection of the presence of liquid.

While the point level sensors of DE68903015T2 and Sakharov are purely based on Lamb waves travelling inside the vessel walls, the point level sensor of RU2112221C1 emits both a Lamb wave into the vessel wall and a longitudinal ultrasound wave into the liquid. Both waves propagate horizontally and in parallel to the liquid surface. By measuring the attenuation of the two signals, a more reliable and accurate result is obtained.

In Sakharov, it is described that for generation and detection of the Lamb waves, the acoustic transducers were attached to acoustic wedges made of polyurethane. The acoustic transducer would generate a bulk longitudinal wave, which would then be transformed into Lamb waves by the polyurethane wedge. The wedge angle θ between the surface of the vessel wall and the direction of the emitted and received Lamb wave is chosen so as to satisfy the condition $\cos\theta = v_B/v_L$, where $V_B$ is the velocitiy of bulk longitudinal waves in the wedge, and is the velocity of Lamb waves in the vessel wall.

It is an object of the present invention to provide an alternative method and an alternative system for non-intrusively and continuously measuring the height of a liquid surface in a vessel.

This objective is achieved by a system and a method according to the independent claims.

As is known for example from above described Sakharov, the system comprises an ultrasonic transmitter for generating an ultrasound wave and for emitting it into the vessel wall, an ultrasonic receiver for receiving the ultrasound wave through the vessel wall, at least one electronic control and data processing unit for controlling operation of the transmitter and of the receiver, for determining a time of flight of the ultrasound wave and for determining the liquid level from the time of flight.

According to the invention, the transmitter is a frequency-tunable transmitter which is placed at a first position at the outside of the vessel wall and below the level of the liquid surface in such a way that the transmitter is able to emit the ultrasound wave as a primary Lamb wave into the vessel wall so that a part of the primary Lamb wave leaks from the vessel wall into the liquid in form of a pressure wave in an inclined and upward direction towards the liquid surface. The receiver is placed at a second position at the outside of the vessel wall and below the level of the liquid surface in such a way that the receiver is able to receive a secondary Lamb wave which is generated by the pressure wave hitting the vessel wall after having been reflected by the liquid surface. The at least one electronic control and data processing unit is adapted to control the transmitter (38, 48) to emit the primary Lamb wave (30) at different frequencies
for each of the different frequencies, to determine the time of flight of the pressure wave and/or the amplitude of the received secondary Lamb wave,
to change the frequency of the transmitter until the determined time of flight reaches a minimum or until the determined amplitude reaches a maximum, and
to determine the liquid level based on the relationship that the minimum time of flight or the time of flight corresponding to the maximum amplitude of the secondary Lamb wave, respectively, equals the length of the travel path of the pressure wave divided by the speed of the pressure wave in the liquid.

The term "time of flight" relates to the time which elapses between emission and reception of a signal.

With the phrase "inclined and upward direction" it is required that the radiation angle between the pressure wave and a horizontal axis is between zero and ninety degrees.

Further, it is to be noted that the at least one electronic control and data processing unit of the proposed system is adapted to perform all the steps of the various methods described in the following, for obtaining measurements and for determining the various magnitudes which it then uses for generating the liquid level as an output result.

The basic idea behind the invention is to send an ultrasound signal through a tank or vessel wall under an angle towards the liquid surface where it is reflected, and to detect the reflection of the ultrasound signal on an adjacent or on the opposite vessel wall. The angle of the ultrasound signal is controlled within a certain range by making use of the characteristic of a leaky Lamb wave that the radiation angle of the pressure wave emitted into a liquid from a solid wall changes with the frequency of the Lamb wave. Accordingly, the transmitter is choen to be a frequency tunable transmitter of Lamb waves, and the receiver is adapted accordingly.

During the measurement procedure, the radiation angle of the emitted ultrasound waves is varied as a function of frequency or wave length to find the minimal time between emitting and receiving the signal or to find the maximum amplitude in the received signal. The speed of sound in the liquid is either assumed to be known and constant, or it is determined before measuring the liquid level.

Instead of a single transmitter and a single receiver, two transducers may be used, where each transducer contains both a transmitter and a receiver. This may be advantageous when determining the speed of sound in the liquid.

The generation of Lamb waves in the vessel wall with varying frequency or varying wave length can be achieved in different ways.

The transmitter can be a piezo-electric transmitter or an electromagnetic acoustic transmitter, which preferably may be mounted on a wedge. In that case, in order to ensure that the receiver is selective to a certain direction only and therefore receives only those ultrasound signals that belong to the reflected pressure wave and accordingly arrive under a certain range of angles, also the receiver is attached to the vessel wall via a wedge.

Alternatively, a piezo-electric transmitter may be used in combination with a mechanical grid which is placed directly in front of it or in combination with an electronic grid resulting in a so called interdigital transmitter that consists of comb shaped electrodes.

The invention and its embodiments will become more apparent from the example and its embodiments described below in connection with the appended drawings which illustrate.

As explained above, the liquid level measurement presented here is based on the usage of Lamb waves. FIG. 2 shows the two fundamental zero-order modes of a Lamb wave propagating in a plate or wall having a thickness d. As can be seen, the symmetrical zero-order mode S0 moves inside the plate in a symmetrical fashion with respect to the median plane of the plate positioned at half the thickness d/2. The symmetrical zero-order mode S0 is also called the extensional mode because the wave stretches and compresses the plate in the wave motion direction. For the asymmetrical zero-order mode A0, the plate bends as its upper and lower surfaces move in the same direction. The asymmetrical zero-order mode A0 is also called the flexural mode because most of the wave's movement takes place in a normal direction to the plate, and only little motion occurs in the direction parallel to the plate.

Figure 3:
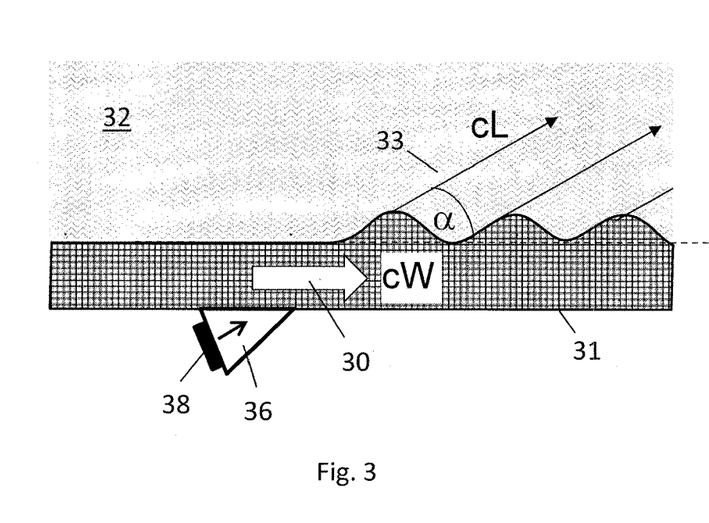
FIG. 3 the principle of generating an angular pressure wave in a liquid via a wedge transmitter.

In FIG. 3, it is shown what happens when the plate 31 comes in contact with a liquid 32. In that case, the reflectivity of the plate's outer surface towards liquid 32 is reduced and the Lamb wave 30 emits acoustic energy in form of a pressure wave 33 into the liquid 32. This occurs especially for the asymmetric mode A0 at low frequencies. In this situation, the Lamb wave becomes a leaky Lamb wave.

The emitted acoustic energy is sent as a more directional acoustical signal into the liquid. The direction at which the signal is emitted is hereby determined by the speed of sound in the wall and by the speed of sound in the liquid according to $$\cos(\alpha) = cL/(cW(f)), \quad (2),$$

as can be seen from FIG. 3, where $\alpha$ is the angle between the wall 31 and the pressure wave 33, cL is the speed of sound in the liquid 32 and cW (f) is the possibly frequency-dependent phase velocity of the Lamb wave 30, also called the primary Lamb wave, in the wall.

In case of varying the speed of sound of the Lamb wave in the wall, the emitted beam direction will also be varied. By choosing a Lamb mode with a frequency dependent speed of sound, the direction of the emitted beam can easily be changed by varying the frequency of the emitted Lamb waves.

The zero-order asymmetric mode A0 is a good choice for the level measurement purposes described here, since it ensures an efficient radiation of acoustic energy into the liquid over a broad range of frequencies. Apart from that, the propagation speed of the A0-mode is strongly frequency dependent. But also other modes can be used if they have these same properties.

In FIG. 3, it is also shown that ultrasonic transmitter 38 is mounted on a wedge 36 which is attached to the outside or dry side of the plate 31. In this way, it is predetermined in what general direction the pressure wave 33 in the liquid 32 can be emitted, with the exact angle of the emitted pressure wave 33 then altering around that general direction depending on the chosen frequency according to equation 2.

Figure 4:
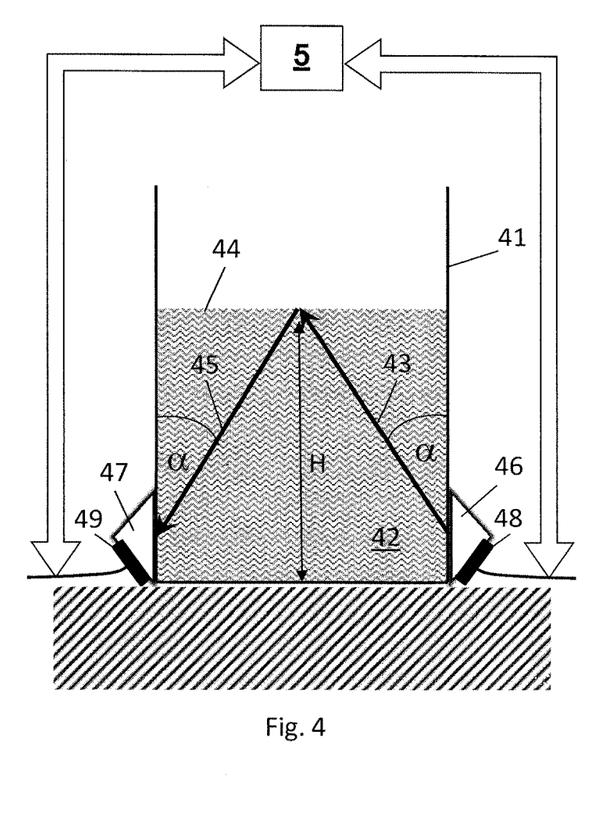
FIG. 4 a first embodiment for measuring the liquid level.

In FIG. 4, a first embodiment is shown of a system for measuring the liquid level in a vessel 41 continuously and non-intrusively. An ultrasonic transmitter 48 is mounted on a first wedge 46 for generating an ultrasound wave and for emitting it into the vessel wall. An ultrasonic receiver 49 is mounted on a second wedge 47 for receiving the ultrasound wave through the vessel wall. At least one electronic control and data processing unit 6 is arranged for controlling operation of the transmitter 48 and of the receiver 49 and for determining the liquid level H from a time of flight of the ultrasound wave. The at least one electronic control and data processing unit 6 can either be a stand-alone unit or it can be integrated in the transmitter 48 and/or in the receiver 49.

The transmitter 48 is a frequency-tunable transmitter, preferably a piezo-electric transmitter or an electromagnetic acoustic transmitter, which is placed together with the first wedge 46 at a first position ([h1, d1], see FIG. 6) at the outside of the vessel wall and below the level of the liquid surface 44 in such a way that the transmitter 48 is able to emit the ultrasound wave as a primary Lamb wave (30) into the vessel wall so that a part of the primary Lamb wave leaks from the vessel wall into the liquid in form of a pressure wave 43 in an inclined and upward direction, at a certain angle $\alpha$, towards the liquid surface 44.

The receiver 49 is placed together with the second wedge 47 at a second position ([h2, d2], see FIG. 6) at the outside of the vessel wall and below the level of the liquid surface 44 in such a way that the receiver 49 is able to receive a secondary Lamb wave which is generated by the reflection 45 of the pressure wave 43 hitting the vessel wall, wherein the original pressure wave 43 is reflected by the liquid surface 44. The process of receiving the reflection of the pressure wave is the same as shown in FIG. 3 for emitting the pressure wave, just with opposite directions. Accordingly, the pressure wave 33 of FIG. 3 would become the reflection of the pressure wave moving towards the plate 31 (or vessel wall), and hitting the plate at angle $\alpha$, where it would generate the secondary Lamb wave propagating inside the plate (or vessel wall) towards the wedge of the receiver.

The at least one electronic control and data processing unit 6 is adapted to repeatedly determine the time of flight t of the pressure wave 43, 45, to change the ultrasonic frequency f of the transmitter 48 until the determined time of flight reaches a minimum $t_{min}$ or the amplitude of the secondary Lamb wave received by the receiver 49 reaches a maximum, and to determine the liquid level H based on the relationship that the minimum time of flight $t_{min}$ or the time of flight of the signal having the maximum amplitude in the secondary Lamb wave equals the length of the travel path (a1+a2, see FIG. 5) of the pressure wave 43, 45 divided by the speed of the pressure wave in the liquid cL.

Figure 5:
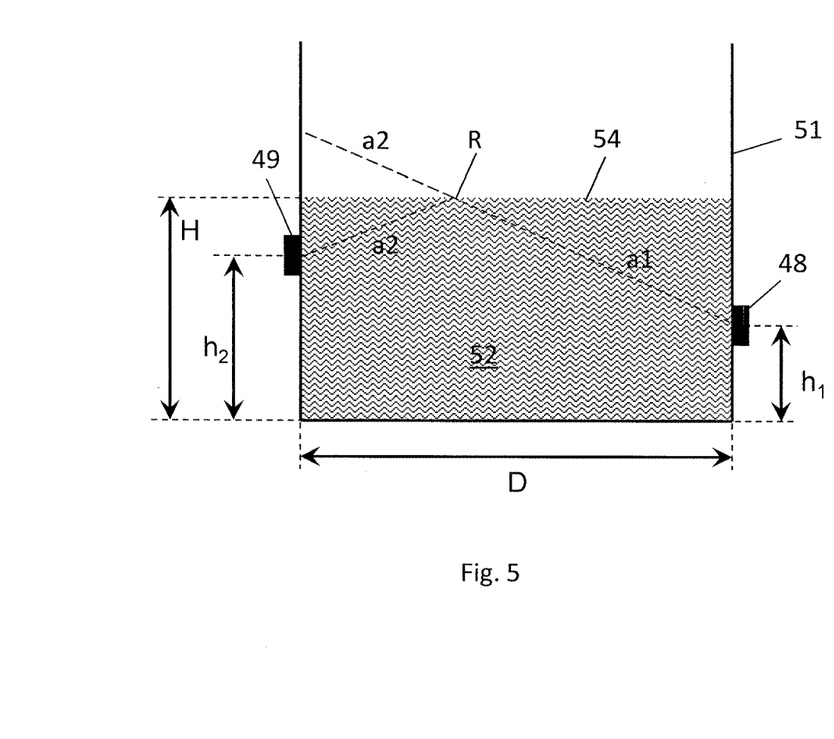
FIG. 5 the geometric relations of the first embodiment.

In FIG. 5, the geometric relations of the first embodiment are depicted, wherein in the first embodiment the transmitter 48 and receiver 49 are placed at directly opposite parts of the wall of vessel 51 and at different heights h1 and h2. Accordingly, the distance between the positions of transmitter 48 and receiver 49 equals the outer diameter D of vessel 51. For simplicity, the method is illustrated here with a vessel of cylindrical shape. However, the method may be applied to any other shape of vessel as well. In a more general, second embodiment shown in FIG. 6, transmitter 48 and receiver 49 are not placed at directly opposite parts of the wall of vessel 51 but at a certain distance d1 and d2, respectively, away from the outer diameter D. Accordingly, the wedges 46 and 47 need to be shaped accordingly, for example by having an inclination in more than one direction, in order to ensure that the reflection 45 of pressure wave 43 is received by receiver 49. When comparing FIGS. 5 and 6, it may be noted that in FIG. 5 the transmitter 48 is positioned in the horizontal direction at d1=0, and the receiver 49 at d2=D.

Figure 6:
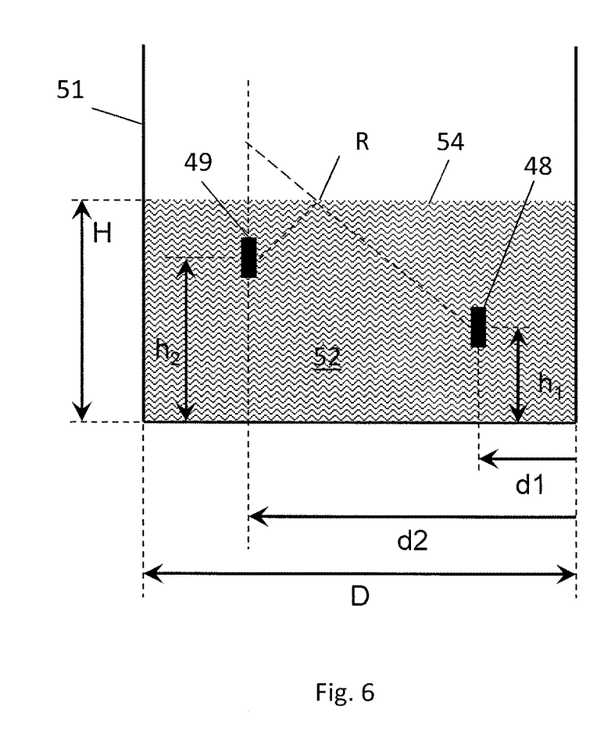
FIG. 6 a second embodiment for measuring the liquid level.

From FIGS. 2, 5 and 6, it can be understood that the at least one electronic control and data processing unit 6 may be adapted to determine the length of the travel path a1+a2 of pressure wave 43, 45 from the geometric dimensions of a triangle which is formed between the first position [d1, h1], the second position [d2, h2] and the point R at which the pressure wave 43 is reflected by the liquid surface 54.

As explained above, the transmitter 48 together with the first wedge 46 is adapted to emit a primary Lamb wave (30) having a dominant asymmetric zero-order mode A0, part of which is leaked into the liquid as the pressure wave 43. By changing via electronic control and data processing unit 6 the frequency of the excitation of transmitter 48, the direction of the emitted pressure wave 43 in the liquid 42 is altered based on the frequency-dependent phase velocity of the asymmetric zero-order mode A0, until the determined time of flight of pressure wave 43 and its reflection 45 reach a minimum tmin.

For the first embodiment (see FIG. 5), the liquid level H (also called the filling level) can then be determined from the equation $$tmin*cL = \sqrt{D^2 + (2H - h1 - h2)^2} \quad (2).$$

For the second embodiment (see FIG. 6), the liquid level H can be determined from the more general equation $$tmin*cL = \sqrt{(d2-d1)^2 + (2H - h1 - h2)^2} \quad (3).$$

As already mentioned, the speed cL of the pressure wave 43, 45 in the liquid 42 may either be assumed to be known and constant, or it may be determined before measuring the liquid level H during a speed of sound calibration.

The latter will be explained in the following in connection with FIGS. 7 to 10.

It was recognized that the speed of sound depends on the medium and varies with the temperature. For example, the speed of sound varies for liquids from 943 m/s for carbon tretrachloride (C Cl4) to 1660 m/s for aniline, which corresponds to a variation of about 70%. In water, the temperature variation is again about 1800 ppm/K at room temperature.

In those metals which are commonly used as a material for vessel walls, the speed of sound varies depending on whether the acoustic signal inside the wall is a longitudinal wave or a shear wave. For longitudinal waves, the speed of sound in steel is 5400 m/s, in aluminum 5100 m/s and in Invar, which is a Ni/Fe alloy, 4300 m/s. This corresponds to a variation of 25%. For shear waves, the speed of sound in steel is 3200 m/s, in aluminum 3100 m/s and in Invar 2700 m/s, which corresponds to a variation of 18%. The temperature variation in wall metals is 150 ppm/K.

Accordingly, it can be observed that a considerable change may occur in the speed of sound of a liquid medium depending on the temperature and chemical composition of the medium, so that the speed of sound needs to be individually determined before measuring the level of the liquid in a vessel.

Figure 7:
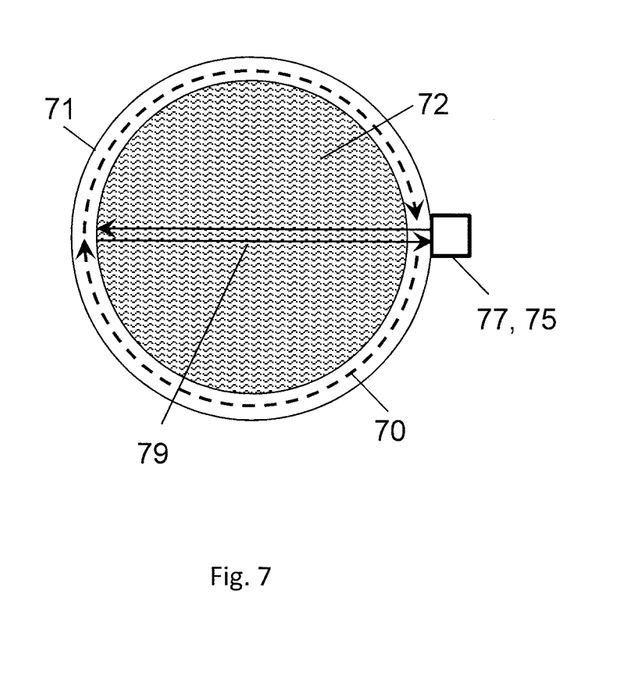
FIG. 7 a first embodiment for measuring the speed of sound in the liquid.
Figure 8:
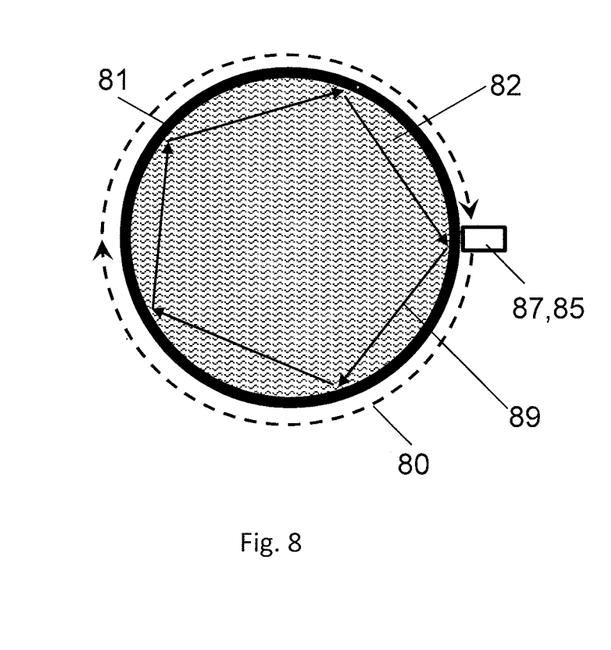
FIG. 8 a second embodiment for measuring the speed of sound in the liquid.
Figure 9:
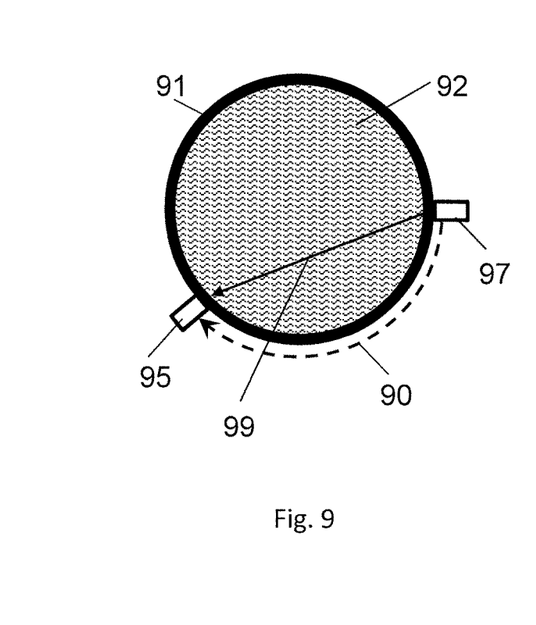
FIG. 9 a third embodiment for measuring the speed of sound in the liquid.

FIGS. 7, 8 and 9 each show a view from the top of a vessel 71, 81, 91 for measuring the speed of sound in a liquid 72, 82, 92 contained in the vessel. An acoustic transmitter 77, 87, 97 is mounted below the liquid surface and at the outside of the vessel 71, 81, 91 for transmitting a direct acoustic signal 79, 89, 99 into the liquid to travel inside a first travelling plane towards an acoustic receiver 75, 85, 95. Advantageously, the acoustic transmitter and receiver are the same as used for the later liquid level measurement (see FIG. 9). However, in the embodiments of FIGS. 7 and 8, only one transducer with integrated transmitter and receiver is needed for the speed of sound calibration. Accordingly, either the transmitter 48 or the receiver 49 or both may be part of a transducer, which transducer may then be used for calibrating the speed of sound in the liquid 42. As a result, the embodiments of FIGS. 2, 5 and 6 would each include at least one additional receiver for performing the speed of sound calibration.

The assumed first travelling plane in FIGS. 7, 8 and 9 is a circular plane lying horizontally and in parallel to the bottom of the vessel 71, 81, 91.

The acoustic receiver 75, 85, 95 for receiving the direct acoustic signal 79, 89, 99 is also mounted below the liquid surface. The acoustic receiver 75, 85, 95 is arranged to receive the direct acoustic signal 79, 89, 99 after it has been reflected by the wall of the vessel 71, 81, 91 which lies—at least to some degree—opposite to the wall where the transmitter 77, 87, 97 and the receiver 75, 85, 95 are mounted at. Accordingly, the transmitter 77, 87, 97 is arranged to emit the direct acoustic signal 79, 89, 99 in a direction which is perpendicular to a first reflective surface of the wall of the vessel, so that the direct acoustic signal 29 is reflected back towards its origin and thereby towards the receiver 75, 85, 95.

The transmitter 77, 87, 97 is further arranged to emit an acoustic wall signal 70, 80, 90 in form of an acoustic wave into the wall of the vessel 71, 81, 91 to travel inside the wall of the vessel along a perimeter of the first travelling plane until it is received by the receiver 75, 85, 95.

The at least one electronic control and data processing unit 6 is then further arranged to
  obtain a first time of flight t1 of the direct acoustic signal 79, 89, 99 and a second time of flight t2 of the acoustic wall signal 70, 80, 90 by measuring the period of time between emission and reception of the respective signal;
  obtain a speed of sound cW in the wall of the vessel 71, 81, 91 from a data memory wherein the speed of sound cW in the wall of the vessel is assumed to be known and constant, i.e. it is saved in the data memory in advance as a parameter;
  determine the perimeter P of the first travelling plane, i.e. the perimeter of the circle shown in FIGS. 7, 8, 9, from the speed of sound cW in the vessel wall and from the second time of flight t2;
  determine the length of the travelling path D of the direct acoustic signal 79, 89, 99, which in this case is twice the length of the circle diameter, from the perimeter of the first travelling plane and from an information on the geometric shape of the first travelling plane; and
  determine the speed of sound cL in the liquid 72, 82, 92 from the length of the travelling path of the direct acoustic signal and from the first time of flight t1.

The information on the geometric shape of the first travelling plane is also stored in the data memory, which data memory is preferably integrated in the electronic control and data processing unit.

The perimeter P of the first travelling plane may be determined based on the general relationship P=t2*cW. The length of the travelling path D may be determined in case of a circle diameter based on the general relationship D=2*P/pi, and the speed of sound may be determined based on cL=D/t1. In reality, additional physical effects have to be taken into account, such as delay times occurring in the electronics of transmitter and/or receiver.

Explained differently, FIGS. 7, 8, 9 show that for measuring the speed of sound in a liquid, two acoustical signals are generated, wherein one (79, 89, 99) travels through the medium to the opposite side of the vessel and is reflected back, the other travels along the solid vessel wall, once around the vessel 71, 81, 91. The travel times of the two signals are measured. This solution is based on recognition of the fact that the sound velocity in the solid wall varies much less with the wall material and the temperature than in the liquid inside the vessel. Accordingly, the speed of sound in the vessel wall, cW, is assumed to be known. The travel time in the vessel wall is used together with the assumed speed of sound cW to determine the vessel perimeter and thus the diameter. With the determined vessel diameter, the speed of sound in the liquid can be calculated out of the travel time in the medium.

In FIGS. 7, 8, 9, the direct signal (79, 89, 99) is sent horizontally through the medium to the opposite side of the wall, where it is reflected back and received again at the sender. A second signal (70, 80, 90) is generated as plate wave in the wall and travels through the wall around the circumference of the vessel. The second signal will be also received again at the sender. The travel times of both signals are measured. The time of flight of the direct signal will be used as described above for the speed of sound measurement in the medium (72, 82, 92). The second signal is used for determining the perimeter length of the tank from which then the diameter and thus the traveled distance of the direct signal (79, 89, 99) can be determined.

The length of the perimeter can be determined out of the time of flight of the second signal (20) analogue to equation (1), where again the propagation velocity has to be known, e.g. the speed of sound in the vessel wall. As can be seen from the speed of sound values given above for different wall materials, the variation for the speed of sound between different metals is much lower than for liquids, especially for the shear wave velocity. Also, the variation with the temperature is by a factor of 10 lower compared to liquids. Thus, the uncertainty in the perimeter measurement is lower than if the second signal (70, 80, 90) had been travelling in a liquid medium. Additionally, only a small selection of materials is commonly used as wall material for process vessels and the used wall material is often known. Therefore, when the wall material class is known, the uncertainty will be even lower. Also, the temperature of the wall is easier to determine than the temperature of the liquid, e.g. it can be measured by surface temperature sensors, and thus also the temperature dependency of the propagation velocity or speed of sound can be further compensated by a known temperature dependency of the wall material. Consequently, the uncertainty in the value of the speed of sound cL in the liquid used for the level measurement is reduced to the uncertainty of the speed of sound of the wall material.

The embodiment of FIG. 9 differs from the embodiment of FIG. 7 in that the first acoustic signal 99 is not reflected back from the opposite vessel wall, to reduce the travel distance in case of a liquid 92 with a high damping factor. In the system of FIG. 3, the transmitter 97 is arranged to emit the direct acoustic signal 99 in an angular direction which is not perpendicular to a first reflective surface of the wall of the vessel, so that the first acoustic signal 99 travels straight towards the receiver 95. Accordingly, the generated signal (99) for the speed of sound calibration does not need to travel over the full tank diameter/perimeter. In case that no difference is made between transmitter and receiver, but that transducers are used which have both emitting and receiving capability, an additional transducer may be used at a second point of the vessel's perimeter. In the same manner as shown in FIG. 9, the signal for the sound calibration (99) can be directed towards this second transducer and has to travel only a shorter distance. The second signal traveling through the vessel wall, i.e. the acoustic wall signal 90, would also be received by this second transducer and would also have to cover a shorter path only. This would be of advantage in case of high damping in either the liquid 92 or the wall of vessel 91 or both, or in case that an installation part in the vessel 91 would block a path straight through the middle of the vessel 91.

The embodiment shown in FIG. 8 differs from the embodiment of FIG. 7 in that the direct acoustic signal 89, which is to travel through the liquid 82, is not sent out straight to the receiving side, but under an angle. It is then reflected several times along the vessel wall. With this embodiment, again problems with installations in the middle of the vessel 81 are avoided, i.e. blocking parts in the middle of the tank are no longer of concern. In the system of FIG. 8, the transmitter 87 and the receiver 85 are integrated in the same device and are mounted at the outside of the wall of vessel 81. The transmitter 87 is arranged to emit the direct acoustic signal 89 in an angular direction which is not perpendicular to a first reflective surface of the wall of the vessel, so that the first acoustic signal 89 is reflected more than once by the wall of the vessel 81 before it is received by the receiver 85.

In summary of the descriptions of the embodiments of FIGS. 7 to 9, it can be noted that the direct acoustic signal is received by the receiver either directly (FIG. 9) or as a reflection of it (FIGS. 7, 8). Further, the vessels are all assumed to have a cylindrical shape at least in the area where the measurement of the speed of sound is performed. In FIGS. 7 to 9, the view is always shown from the top of the vessel. Due to the cylindrical shape at the height of the speed of sound measurements, the walls of the vessels 71, 81, 91 are all shown as circles. However, the solution proposed here is applicable to any other geometric form as long as this form allows for the travel length of the direct acoustic signal to be obtained when knowing the perimeter of the plane across which the direct acoustic signal propagates.

In the following, a further development of the embodiments of FIGS. 7 to 9 is described, where the transmitter 77, 87, 97 is arranged to emit the acoustic wall signal as a Lamb wave with a symmetric zero-order mode S0 and an asymmetric zero-order mode A0. The frequency behavior of these different Lamb wave modes is used to take into account as a further vessel parameter the wall thickness, so as to determine the speed of sound in the wall of the vessel with a higher precision.

The acoustic waves which are emitted by the transmitter 77, 87, 97 which propagate in the vessel wall are called plate or Lamb waves. As explained above, these waves occur in different kinds of modes each having a different speed of sound and a different dependency of the speed of sound on the frequency f that also depends on the thickness d of the wall.

Figure 10:
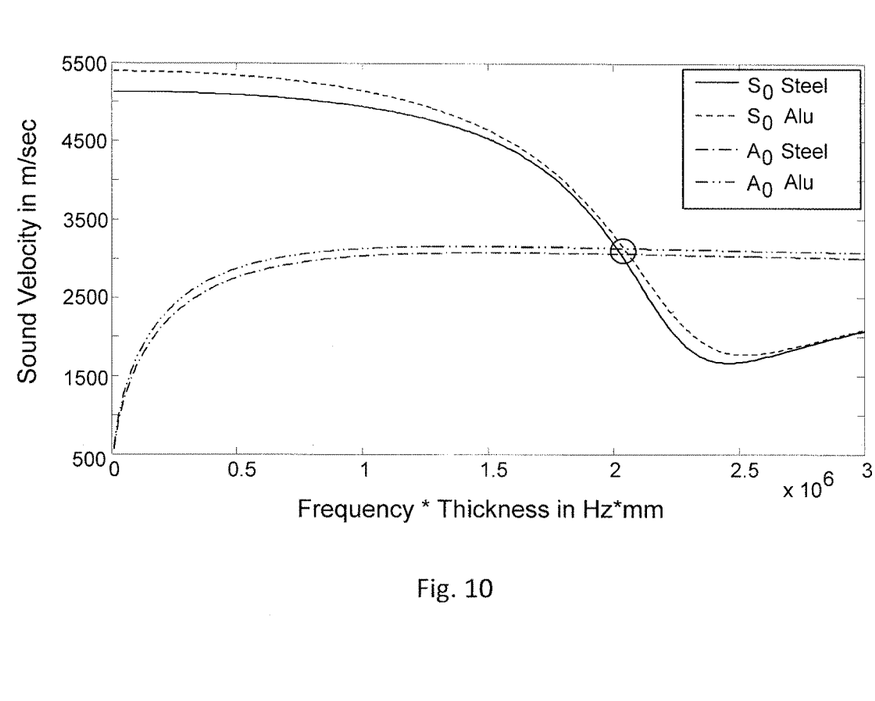
FIG. 10 a dependency of speed of sound from wall thickness, wall material and signal frequency.

The dependency of the speed of sound or sound velocity of the two fundamental modes S0 and A0 from the frequency multiplied by the wall thickness is shown in FIG. 10 for the group velocity, where different graphs are depicted for the two wall materials aluminum and steel.

In FIG. 10, it is emphasized that the dependency of the Lamb wave's speed of sound from the frequency is coupled to its dependency from the wall thickness. This combined frequency/thickness dependency is described by the product out of frequency and thickness f*d, which is depicted in FIG. 10 on the x-axis of the diagram.

Assuming an invariable thickness, it can be seen from FIG. 10 that the sound velocity of the S0 mode is almost constant for low frequencies. The values between 5000 and 5500 m/s correspond to the above given sound velocities of a longitudinal wave in an aluminum or steel bulk material, respectively. For higher frequencies, the speed of sound of the S0 mode decreases.

The sound velocity of the A0 mode increases with the frequency up to the value of about 3000 m/s, given above as the shear velocity in an aluminum or steel bulk material. At higher frequencies, the speed of sound of the A0 mode remains nearly constant. At higher frequencies, also the difference between the sound velocity of steel and aluminum for the A0 mode is comparatively low. It would thus be of advantage to use for the acoustic wall signal 70, 80, 90 a frequency in this higher frequency range.

The symmetric S0 mode also shows for higher frequencies, when the speed of sound decreases, a quite similar behavior for the different materials, resulting in the sound velocity for the different materials to be quite similar in the higher frequency*thickness range. This is another reason why this frequency*thickness range would be interesting to be used for further decreasing the uncertainty in the sound velocity.

Because the exact wall thickness is often not known a priori and because the sound velocity of the different modes depends on the frequency*thickness product, the graph shown in FIG. 10 can be made use of. To do that it needs to be known in which part or at which point in the c(f*d) curve of FIG. 10 the correct sound velocity in the wall can be obtained. For simple measurements as described above, a low frequency can be chosen in case of a measurement with the symmetric S0 mode, or a high frequency can be chosen in case of a measurement with the asymmetric A0 mode, where the respective frequency is chosen in such a way that for all values of wall thickness which are to be expected the resulting product of frequency and wall thickness would still result in a sound velocity belonging to the respective constant range in sound velocity.

To further reduce the variance in the speed of sound of the vessel wall material, it is of advantage to use a fixed frequency*thickness value every time a measurement is performed. It has been recognized that an easily detectable frequency*thickness value would be the crossing of the speed of sound values for the two different modes, as indicated in FIG. 10 by the circle. This crossing point would help to stay at a fixed frequency*thickness value in case of an unknown or changing wall thickness. The crossing could be detected by exciting in the transmitters 77, 87, 97 pulses of both propagation modes S0 and A0 with increasing frequencies. When the pulses of the two modes S0 and A0 arrive at the respective receiver 75, 85, 95 at the same time, the crossing point of the two modes is reached. But also other frequency*thickness values can be detected by comparing the frequency behavior of the two modes, as e.g. by comparing the relation of the propagation or speed velocities of the two modes by each other as $c\_S0/c\_A0$. For a given frequency*thickness value this relation would be constant, and by varying the frequency until the relation of the time of flight for the two modes will be inversely equal to this relation of the propagation velocity $t\_A0/t\_S0=c\_S0/c\_A0$, a fixed frequency*thickness value can be obtained.

But also the use of higher order modes is possible to determine specific frequency*thickness values or to get ranges with low sound velocity variances of the wall material.

Additionally, by determining the frequency at which this fixed frequency*thickness value is obtained, the wall thickness may be calculated out of it with the thus known frequency.

In the case of FIG. 8, where the direct acoustic signal 89 is sent out under an angle and is reflected several times along the perimeter until it reaches the receiver 85, the signal travels all the time close to the wall so as to be unaffected by installations in the middle of the vessel 81. Such a path could be generated by using Lamb waves in a similar way as used for the above described perimeter/diameter measurement (acoustic wall signals 70, 80, 90), since certain modes of Lamb waves may radiate acoustic waves from the wall into the liquid, depending on the product frequency*thickness. As already mentioned, this kind of Lamb waves is also called leaky Lamb waves. Leaky Lamb waves occur in the case of the A0 mode at a wide range of frequency*thickness values, when the wall in which the A0 mode propagates is next to a liquid. The direction of the radiated beam is not perpendicular to the wall but under an angle which depends on the sound velocity of the Lamb wave and the sound velocity in the liquid. Thus, by generating Lamb waves with different exciting modes and frequencies the signals for measuring the perimeter/diameter as well as for the sound velocity calibration can be generated.

In the presence of a liquid, the Lamb waves in the wall can be dampened depending on the mode and its frequency*thickness value. Therefore, it is of advantage to perform the perimeter/diameter measurement with the acoustic wall signals 70, 80, 90 at an empty tank. The perimeter/diameter measurement needs only to be done once after the installation and can then be used for the further measurements of the speed of sound in the liquid and of the liquid level.

The invention claimed is:
1. A system for non-intrusive and continuous level measurement of a liquid, where the liquid is enclosed by a solid wall of a vessel, the system comprising
   an ultrasonic transmitter for generating an ultrasonic wave and for emitting it into the vessel wall,
   an ultrasonic receiver for receiving the ultrasound wave through the vessel wall,
   at least one electronic control and data processing unit for controlling operation of the transmitter and of the receiver and for determining the liquid level from a time of flight of the ultrasound wave,
   wherein
   the transmitter is a frequency-tunable transmitter which is placed at a first position at the outside of the vessel wall and below the level of the liquid surface in such a way that the transmitter is able to emit the ultrasound wave as a primary Lamb wave into the vessel wall so that a part of the primary Lamb wave leaks from the vessel wall into the liquid in form of a pressure wave in an inclined and upward direction towards the liquid surface,
   the receiver is placed at a second position at the outside of the vessel wall and below the level of the liquid surface in such a way that the receiver is able to receive a secondary Lamb wave which is generated by the pressure wave hitting the vessel wall after having been reflected by the liquid surface , the at least one electronic control and data processing unit is adapted
to control the transmitter to emit the primary Lamb wave at different frequencies,
for each of the different frequencies, to determine the time of flight of the pressure wave and/or the amplitude of the received secondary Lamb wave,
to change the frequency of the transmitter until the determined time of flight reaches a minimum or until the determined amplitude reaches a maximum, and
to determine the liquid level based on the relationship that the minimum time of flight or the time of flight corresponding to the maximum amplitude of the secondary Lamb wave, respectively, equals the length of the travel path of the pressure wave divided by the speed of the pressure wave in the liquid.

2. The system according to claim 1, wherein the at least one electronic control and data processing unit is adapted to determine the length of the travel path from the geometric dimensions of a triangle which is formed between the first position, the second position and the point at which the pressure wave is reflected by the liquid surface.

3. The system according to claim 2, wherein the transmitter is mounted on a first wedge and together with the first wedge is adapted to emit the primary Lamb wave having a dominant asymmetric zero-order mode, part of which is leaked into the liquid as the pressure wave.

4. The system according to claim 2, wherein the transmitter is a piezo-electric transmitter or an electromagnetic acoustic transmitter.

5. The system according to claim 1, wherein the transmitter is mounted on a first wedge and together with the first wedge is adapted to emit the primary Lamb wave having a dominant asymmetric zero-order mode, part of which is leaked into the liquid as the pressure wave.

6. The system according to claim 5, wherein the receiver is mounted on a second wedge and together with the second wedge is adapted to receive the secondary Lamb wave which is generated by the primary Lamb wave with dominant asymmetric zero-order mode after its corresponding pressure wave has been reflected by the liquid surface and has hit the vessel wall.

7. The system according to claim 5, wherein the transmitter is a piezo-electric transmitter or an electromagnetic acoustic transmitter.

8. The system according to claim 1, wherein the transmitter is a piezo-electric transmitter or an electromagnetic acoustic transmitter.

9. A method for non-intrusive and continuous level measurement of a liquid, where the liquid is enclosed by a solid wall of a vessel, the method comprising the steps
generating an ultrasound wave and emitting it into the vessel wall by using an ultrasonic transmitter,
receiving the ultrasonic wave through the vessel wall by using an ultrasonic receiver,
controlling operation of the transmitter and of the receiver and determining the liquid level from a time of flight of the ultrasound wave by using at least one electronic control and data processing unit,
wherein
emitting the ultrasound wave via the transmitter as a primary Lamb wave into the vessel wall below the liquid surface so that a part of the primary Lamb wave leaks from the vessel wall into the liquid in form of a pressure wave in an inclined and upward direction towards the liquid surface, wherein the transmitter is a frequency-tunable transmitter placed at a first position at the outside of the vessel wall,
receiving via the receiver a secondary Lamb wave which is generated by the pressure wave hitting the vessel wall after having been reflected by the liquid surface, wherein the receiver is placed at a second position at the outside of the vessel wall and below the liquid surface,
via the at least one electronic control and data processing unit:
controlling the transmitter to emit the primary Lamb wave at different frequencies,
for each of the different frequencies, determining the time of flight of the pressure wave and/or the amplitude of the received secondary Lamb wave,
changing the frequency of the transmitter until the determined time of flight reaches a minimum or until the determined amplitude reaches a maximum, and
determining the liquid level based on the relationship that the minimum time of flight or the time of flight corresponding to the maximum amplitude of the secondary Lamb wave, respectively, equals the length of the travel path of the pressure wave divided by the speed of the pressure wave in the liquid.

10. The method according to claim 9, wherein the length of the travel path is determined from the geometric dimensions of a triangle which is formed between the first position, the second position and the point at which the pressure wave is reflected by the liquid surface.

11. The method according to claim 10, wherein the speed of the pressure wave in the liquid is determined by the following steps:
transmitting a direct acoustic signal into the liquid to travel inside a first travelling plane, receiving the direct acoustic signal, and determining its time of flight as a first time of flight;
emitting an acoustic wall signal in form of an acoustic wave into the wall of the vessel to travel inside the wall of the vessel along a perimeter of the first travelling plane until it is received, and determining its time of flight as a second time of flight;
obtaining a speed of sound in the vessel wall from a data memory, wherein the speed of sound in the vessel wall may be a predetermined value or a measured value;
determining the perimeter of the first travelling plane from the speed of sound in the vessel wall and from the second time of flight;
determining the length of the travelling path of the direct acoustic signal from the perimeter of the first travelling plane and from an information on the geometric shape of the first travelling plane obtained from the data memory;
determining the speed of sound in the liquid from the length of the travelling path of the first acoustic signal and from the first time of flight.

12. The method according to claim 9, wherein the speed of the pressure wave in the liquid is determined by the following steps:
transmitting a direct acoustic signal into the liquid to travel inside a first travelling plane, receiving the direct acoustic signal, and determining its time of flight as a first time of flight;
emitting an acoustic wall signal in form of an acoustic wave into the wall of the vessel to travel inside the wall of the vessel along a perimeter of the first travelling plane until it is received, and determining its time of flight as a second time of flight;

obtaining a speed of sound in the vessel wall from a data memory, wherein the speed of sound in the vessel wall may be a predetermined value or a measured value;

determining the perimeter of the first travelling plane from the speed of sound in the vessel wall and from the second time of flight;

determining the length of the travelling path of the direct acoustic signal from the perimeter of the first travelling plane and from an information on the geometric shape of the first travelling plane obtained from the data memory;

determining the speed of sound in the liquid from the length of the travelling path of the first acoustic signal and from the first time of flight.

13. The method according to claim 12, wherein the direct acoustic signal is emitted in a direction which is perpendicular to a first reflective surface of the wall of the vessel.

14. The method according to claim 13, wherein the acoustic wall signal is emitted as a Lamb wave with a symmetric zero-order mode and an asymmetric zero-order mode.

15. The method according to claim 12, wherein the acoustic wall signal is emitted as a Lamb wave with a symmetric zero-order mode and an asymmetric zero-order mode.

16. The method according to claim 7, wherein in case that the thickness of the vessel wall is known, the speed of sound in the vessel wall is obtained from a graph of speed of sound in the wall material versus the mathematical product of wave frequency and wall thickness and stored in the data memory, by choosing as wave frequency for the symmetric or the asymmetric zero-order mode a frequency which in the graph belongs to a range of approximately constant speed of sound in the wall material, and wherein the symmetric or the asymmetric zero-order mode is emitted at the respectively chosen wave frequency.

17. The method according to claim 16, wherein the symmetric zero-order mode and the asymmetric zero-order mode are emitted with increasing frequency and wherein the specific frequency is detected at which the symmetric zero-order mode and the asymmetric zero-order mode are received simultaneously, and wherein a value for the speed of sound in the wall of the vessel is stored in the data memory which corresponds to the overlapping of a graph of speed of sound versus the mathematical product of wave frequency and wall thickness for the symmetric zero-order mode with the same type of graph for the asymmetric zero-order mode.

18. The method according to claim 7, wherein in case that the thickness of the vessel wall is unknown, the speed of sound in the vessel wall is obtained from a graph of speed of sound in the wall material versus the mathematical product of wave frequency and wall thickness and stored in the data memory, by choosing as wave frequency for the symmetric or the asymmetric zero-order mode a frequency which for all to be expected values of wall thickness would result in a product of wave frequency and wall thickness which in the graph belongs to a range of approximately constant speed of sound in the wall material, and wherein the symmetric or the asymmetric zero-order mode is emitted at the respectively chosen wave frequency.

19. The method according to claim 7, wherein the symmetric zero-order mode and the asymmetric zero-order mode are emitted with increasing frequency and wherein the specific frequency is detected at which the symmetric zero-order mode and the asymmetric zero-order mode are received simultaneously, and wherein a value for the speed of sound in the wall of the vessel is stored in the data memory which corresponds to the overlapping of a graph of speed of sound versus the mathematical product of wave frequency and wall thickness for the symmetric zero-order mode with the same type of graph for the asymmetric zero-order mode.

20. The method according to claim 12, wherein the perimeter of the first travelling plane is determined either when the vessel is empty or at a height of the wall of the vessel which is not in contact with any liquid.

* * * * *